United States Patent [19]

Koseki et al.

[11] Patent Number: 5,225,105
[45] Date of Patent: Jul. 6, 1993

[54] OPTICALLY ACTIVE COMPOUND AND FERROELECTRIC LIQUID CRYSTAL COMPOSITION PRODUCED THEREFROM

[75] Inventors: Eriko Koseki, Kanagawa; Keiichi Nito, Tokyo; Seiichi Arakawa, Kanagawa, all of Japan

[73] Assignee: Sony Corporation, Tokyo, Japan

[21] Appl. No.: 691,408

[22] Filed: Apr. 25, 1991

[30] Foreign Application Priority Data

Apr. 28, 1990 [JP] Japan .................................. 2-112521

[51] Int. Cl.⁵ ...................... C09K 19/12; C09K 19/20; C09K 19/30
[52] U.S. Cl. ....................... 252/299.66; 252/299.63; 252/299.67; 252/299.65
[58] Field of Search ...................... 252/299.63, 299.65, 252/299.66, 299.67

[56] References Cited

U.S. PATENT DOCUMENTS

| | | | |
|---|---|---|---|
| 4,592,858 | 6/1986 | Higuchi et al. | 252/299.66 |
| 4,728,458 | 3/1988 | Higuchi et al. | 252/299.65 |
| 4,737,313 | 4/1988 | Saito et al. | 252/299.63 |
| 4,867,903 | 9/1989 | Nohira et al. | 252/299.63 X |
| 4,871,472 | 10/1989 | Krause et al. | 252/299.65 |
| 4,911,861 | 3/1990 | Higuchi et al. | 252/299.65 |
| 4,911,862 | 3/1990 | Shoji et al. | 252/299.65 |
| 4,914,224 | 4/1990 | Shoji et al. | 560/65 |
| 4,917,821 | 4/1990 | Mori et al. | 252/299.63 |
| 4,921,632 | 5/1990 | Nakamura et al. | 252/299.65 X |

FOREIGN PATENT DOCUMENTS 8705017 12/1987 World Int. Prop. O. .

*Primary Examiner*—Robert L. Stoll
*Assistant Examiner*—C. Harris
*Attorney, Agent, or Firm*—Hill, Steadman & Simpson

[57] ABSTRACT

Disclosed herein is an optically active compound and a ferroelectric liquid crystal composition produced therefrom. The optically active compound has a fluorine atom introduced into the core nucleus so that it does not take on the smectic phase of a high order except for the smectic A phase and smectic C phase and which has carbonyl groups (for dipole) at adequate positions so that it exihibits greater spontaneous polarization. The ferroelectric liquid crystal composition is composed of a chiral component (including the optically active compound) and a non-chiral component, and hence it is superior in response performance.

10 Claims, No Drawings

OPTICALLY ACTIVE COMPOUND AND FERROELECTRIC LIQUID CRYSTAL COMPOSITION PRODUCED THEREFROM

BACKGROUND OF THE INVENTION

1. Field of the Invention

The present invention relates to an optically active compound and a ferroelectric liquid crystal composition produced therefrom which is used as a liquid crystal material for ferroelectric display devices.

More particularly, the present invention relates to a new optically active compound which has a fluorine atom introduced into the core nucleus so that it does not take on the smectic phase of a high order except for the smectic A phase and smectic C phase and which has carbonyl groups (for dipole) at adequate positions so that it exhibits greater spontaneous polarization.

The present invention also relates to a ferroelectric liquid crystal composition capable of quick response which is composed of a chiral component (including said optically active compound) and a non-chiral component.

2. Description of the Prior Art

A recent noticeable liquid crystal material for liquid crystal display devices is a ferroelectric liquid crystal which utilizes the optical switching effect produced by the chiral smectic C phase (referred to as SmC* phase hereinafter). This ferroelectric liquid crystal has several outstanding features: quick response (of the order of microseconds), bistable memory effect, easy time-sharing addressing, and wide view angle.

A ferroelectric liquid crystal has a response time which is given by the formula below.

$$\tau = \eta/P_s E$$

(where $P_s$ represent the spontaneous polarization; $\eta$ represents the viscosity; and E represents the electric field.)

For the response time ($\tau$) to be short, it is desirable that a high voltage be applied and the ferroelectric liquid crystal have a lower value of viscosity ($\eta$) and a greater value of spontaneous polarization ($P_s$).

In general, a ferroelectric liquid crystal for practical use should meet the following requirements.

(1) Great spontaneous polarization.
(2) SmC* phase having a sufficiently long helical pitch, and orientation that can be easily controlled.
(3) Ability to exhibit the SmC* phase over a broad temperature range (including room temperature).
(4) Adequate tilt angle.
(5) Chemical stability.
(6) Low viscosity.
(7) Bistability and a sharp threshold value.

Since there is no single material that meets all of these requirements, it is a common practice to use a mixture of two or more liquid crystals. However, none of the mixtures developed so far meet these requirements, especially (1) and (3).

SUMMARY OF THE INVENTION

The present invention was completed in view of this situation. Therefore, it is an object of the present invention to provide a new optically active compound which exhibits outstanding spontaneous polarization when used in combination with other components. It is another object of the present invention to provide a ferroelectric liquid crystal composition which is characterized by the chiral smectic phase having a broad temperature range, the quick response performance, and the high contrast ratio.

DESCRIPTION OF THE PREFERRED EMBODIMENTS

In order to develop a new liquid crystal material which exhibits great spontaneous polarization and works over a broad range of temperature, the present inventors synthesized a variety of optically active compounds and observed their phase transition temperature and spontaneous polarization they exhibit when they are incorporated into a non-chiral liquid crystal composition. As the result, it was found that a certain kind of optically active compound having a substituted fluorine in the core nucleus exhibits great spontaneous polarization in a mixture with a non-chiral liquid crystal composition. This finding led to the optically active compound of the present invention, which is represented by the formula below.

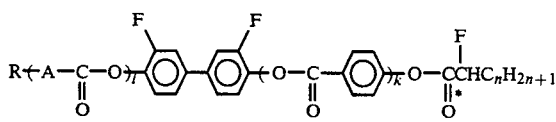

(where R denotes a $C_{6-15}$ alkly group, alkoxyl group, or

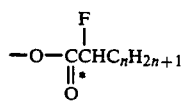

A denotes a benzene ring or cyclohexane ring; 1 and k each denotes 0 or 1; and n denotes an integer of 2 to 15.)

The ferroelectric liquid crystal composition of the present invention is a mixture composed of a chiral component containing this optically active compound and a non-chiral component.

According to the present invention, the optically active compound can be synthesized by the esterification reaction between a monoalkyl ether of 3,3'-difluoro-4,4'-biphenol and a carboxylic acid in which the asymmetric carbon atom at the α position has a substituting fluorine atom. (This carboxylic acid is referred to as an optically active fluorinated carboxylic acid hereinafter.)

The monoalkyl ether of 3,3'-difluoro-4,4'-biphenol can be synthesized according to the following reaction formulas.

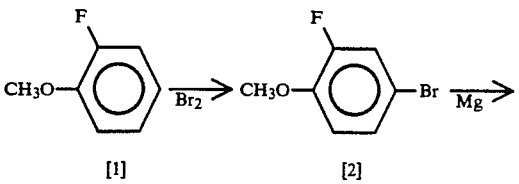

-continued

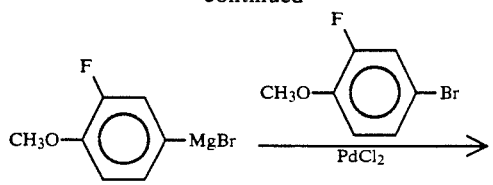
[3]

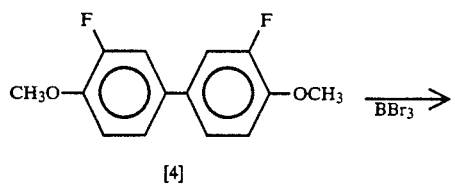
[4]

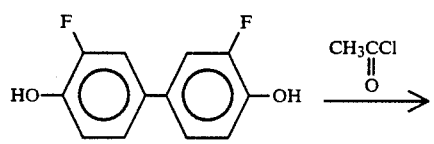
[5]

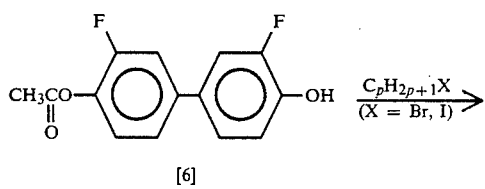
[6]

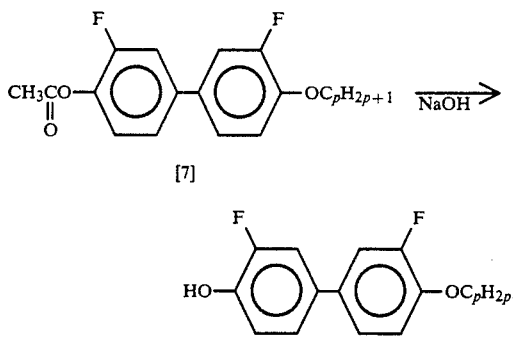
[7]

[8]

The procedure for synthesis is briefly explained below. First, 2-fluoroanisole [1] is reacted with bromine to give 2-fluoro-4-bromoanisole [2], which is subsequently reacted with magnesium to give a compound [3] of Grignard reagent type. This compound is condensed with 2-fluoro-4-bromoanisole [2] in the presence of a palladium chloride catalyst to give 3,3'-difluoro-4,4'-dimethoxybiphenyl [4]. In this way, the biphenyl skeleton is formed. Then, the both terminals of 3,3'-difluoro-4,4,-dimethoxybiphenyl [4] are demethylated by boron tribromide to give 3,3'-difluoro-4,4'-dimethoxybiphenyl [4]. One of the two hydroxyl groups in the compound [5] is blocked by acylation with acetic acid chloride to give a compound [6]. The remaining hydroxyl group in the compound [6] is alkylated with a halogenated alkyl having a specific chain length (p=6 to 15) to give a compound [7]. Finally, the compound [7] undergoes hydrolysis by an alkali catalyst (sodium hydroxide) to remove the acyl group. Thus there is obtained an un- blocked compound [8], which is ready for coupling with a cyclohexane ring through an ester linkage.

On the other hand, the optically active fluorinated carboxylic acid can be synthesized from an optically active amino acid or chiral epoxide by any of the following three methods.

Method A:

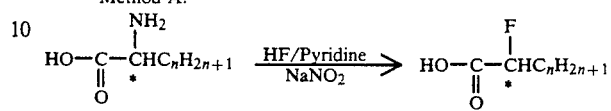

Method B:

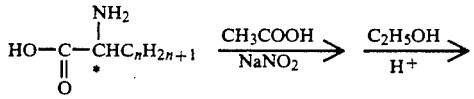

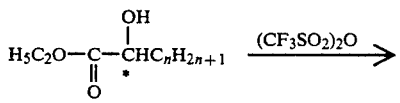

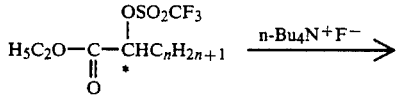

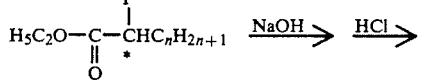

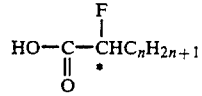

Method C:

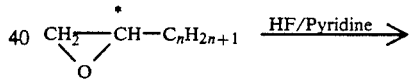

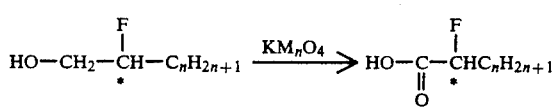

The optically active compound mentioned above constitutes the chiral component to be mixed with a non-chiral component to prepare the ferroelectric liquid crystal composition for actual use which has improved characteristic properties such as orientation and wide useful temperature range.

Examples of the non-chiral component include known liquid crystals (and mixtures thereof) of phenylpyrimidine type, phenylpyridine type, and phenyl benzoate type. One which retains the smectic C phase over a broad temperature range is preferable.

According to the present invention, the optically active compound should be used in an amount of 1-50 wt %, preferably 2-30 wt %, when mixed with a non-chiral component for the preparation of the ferroelectric liquid crystal composition. With an amount less than 1 wt %, it has no marked effect on spontaneous polarization and hence contributes little to response speed. With an amount in excess of 50 wt %, it narrows the useful temperature range.

EXAMPLES

The invention will be described in more detail with reference to the following examples, which are not intended to restrict the scope of the invention.

Example 1

An optically active compound represented by the formula (I) below was synthesized.

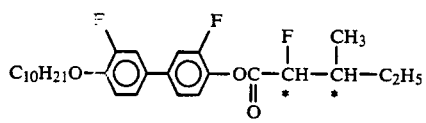

First, L-isoleucine (i) was made into 2-fluoro-3-methylpentanoic acid (v) and a chloride thereof (iv), which is an optically active fluorocarboxylic acid, through the route shown below.

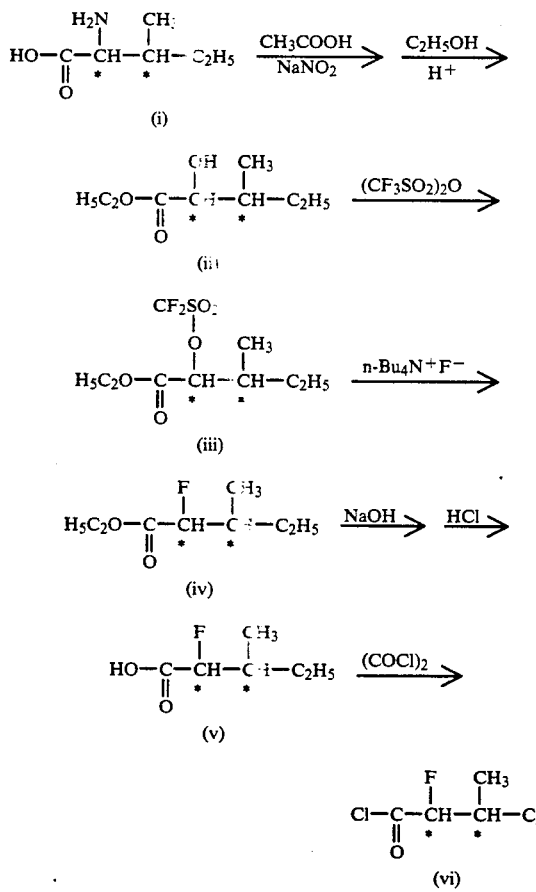

The procedure was started by adding 50 g of L-isoleucine in a mixed solvent composed of 5 ml of hydrochloric acid, 150 ml of acetic acid, and 245 ml of water. The resulting solution was added dropwise with stirring to 400 ml of ice-cooled aqueous solution containing 46 g of sodium nitrite. After standing for 1 hour, the solution was extracted with ether, and the extract was freed of ether by distillation and then purified by vacuum distillation.

To the purified product were added 1.5 g of p-toluenesulfonic acid, 300 ml of ethanol, and 200 ml of toluene. The reactants were heated under reflux for 10 hours during which water was removed by means of a Dean-Stark water separator.

The reaction product was freed of toluene and p-toluenesulfonic acid by atmospheric distillation, and then extracted with ether. The extract was freed of ether by distillation. Thus there was obtained ethyl isoleucinate (ii).

32.8 g of ethyl isoleucinate (ii) was dissolved, together with 40 g of lutidine, in 300 ml of dichloromethane. To the resulting solution was added dropwise 75 g of trifluomethanesulfonic acid anhydride with ice cooling.

The reaction product was diluted with a hexane-ethyl acetate mixture, and the resulting solution was passed through a silica gel column for purification. After solvent removal by vacuum distillation, there was obtained trifluoromethanesulfonate ester of ethyl isoleucinate (iii).

30 g of the compound (iii) was dissolved, together with an equimolar amount of tetrabutylammonium fluoride, in 340 ml of acetonitrile. The resulting solution was allowed to stand overnight at 5° C.

The solution was passed through a silica gel column for purification. After solvent removal by distillation, the residues underwent vacuum distillation. Thus there was obtained ethyl 2-fluoro-3-methylpentanoate (iv).

To 8.5 g of the compound (iv) was added 1N NaOH aqueous solution, followed by stirring at room temperature for 8 hours. The solution was acidified with dilute hydrochloric acid and then extracted with ether. The extract was freed of ether by distillation. Thus there was obtained 2-fluoro-3-methylpentanoic acid (v).

Finally, to the compound (v) was added 10 ml of dichloromethane and then 15 ml of oxalic acid chloride dropwise with ice cooling. The reaction was carried out under reflux at 40° C. for 3 hours. The reaction product was freed of chloromethane and oxalic acid chloride by atmospheric distillation, and the residues were purified by vacuum distillation. Thus there was obtained 2-fluoro-3-methylpentanoic acid chloride (vi), which has a boiling point of 58°–60° C. (at 20 mmHg).

On the other hand, monodecyl ether of 3,3'-difluoro-4,4'-biphenol, which constitutes the central part of the molecule, was synthesized through the following reaction route.

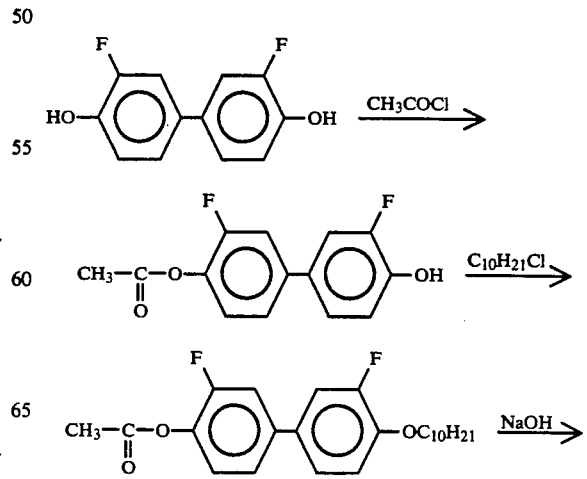

-continued

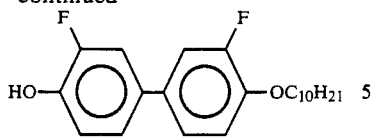

First, 3,3'-difluoro-4,4'-biphenol was dissolved, together with triethylamine, in dioxane, and to the resulting solution was added a dioxane solution of acetic acid chloride. After stirring for about 30 minutes, the reaction product was diluted with water and then extracted with ether. The extract was freed of solvent by distillation, and the residues were dissolved in dimethylformamide. To the solution was added an equimolar amount of NaH (55%). With the solution heated at 60° C., decyl chloride was added and the reaction was carried out under reflux for 4 hours. After cooling, the reaction product was diluted water and allowed to stand overnight in a refrigerator for crystallization. Crystals were filtered out and dissolved in acetone. To the solution was added an aqueous solution of sodium hydroxide, and the solution was heated under reflux for 30 minutes. After dilution with water, the solution was cooled again in a refrigerator for crystallization.

Crystals were filtered out and recrystallized from ethanol to remove didecyl ether of 3,3'-difluoro-4,4'-biphenol (as a by-product). The filtrate was passed through a silica gel column to separate the desired monodecyl ether.

The thus obtained 2-fluoro-3-methylpentanoinc acid chloride (vi) and monodecyl ether of 3,3'-difluoro-4,4'-biphenol were reacted to give the optically active compound (I) in the following manner.

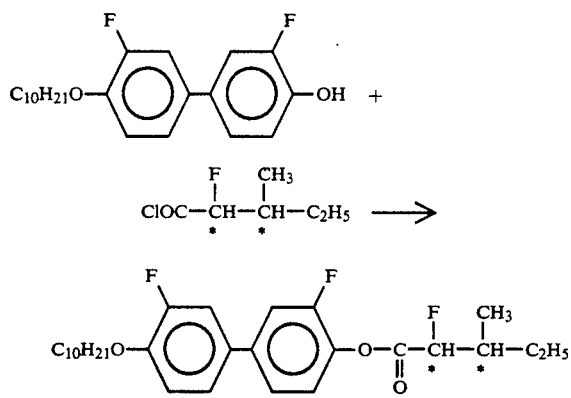

The optically active compound (I) obtained as mentioned above was found to have a phase transition temperature of 47.6° C. for Iso (isotropic liquid) phase →SmA phase, and a phase transition temperature of 39.8° C. for SmA phase →Cr (crystal) phase. Having no chiral smectic C phase, it did not exhibit the spontaneous polarization of its own.

Example 2

An optically active compound represented by the formula (II) below was synthesized.

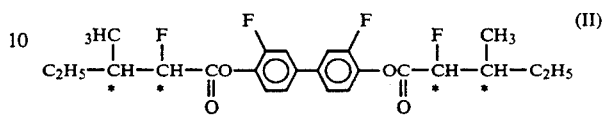

First, L-isoleucine (i) was made into 2-fluoro-3-methylpentanoic acid chloride (iv) and 3,3'-difluoro-4,4'-biphenol was prepared separately in the same manner as in Example 1.

These two compounds were reacted as follows to give the optically active compound (II).

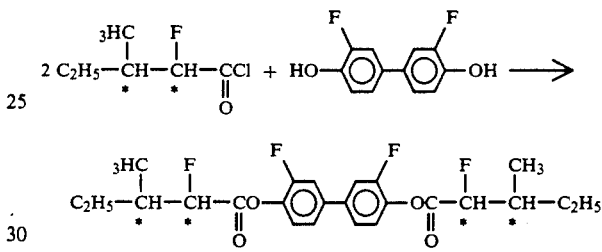

The procedure was started by dissolving 3,3'-difluoro-4,4'-biphenol in dioxane. To the resulting solution was added triethylamine and then 2-fluoro-3methylpentanoic acid chloride dropwise. After dilution with water, the solution was extracted with chloroform. The residues remaining after solvent removal by distillation were passed through a silica gel column (n-hexane/ chloroform) for separation. Upon recrystallization from petroleum ether, there was obtained the optically active compound (II).

The optically active compound (II) obtained as mentioned above was capable of phase transition from Iso (isotropic liquid) phase directly to Cr (crystal) phase at a phase transition temperature of 64.4° C. Having no chiral smectic C phase, it did not exhibit the spontaneous polarization of its own.

Example 3

The optically active compound (I) was synthesized according to the procedure mentioned in Example 1. Then, it was mixed with a non-chiral component to give a ferroelectric liquid crystal composition. The non-chiral component is a mixture of three liquid crystals (A), (B), and (C) represented by the following formulas.

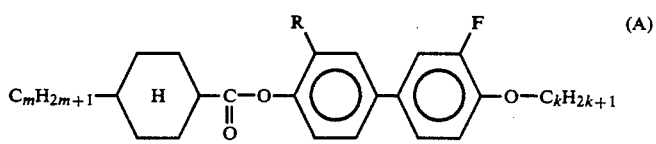

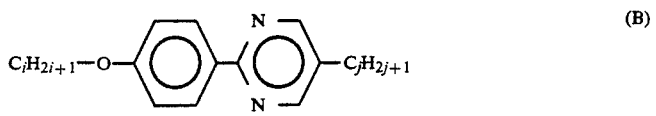

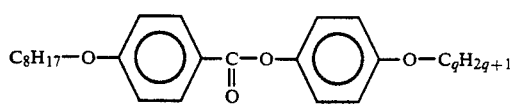
(C)

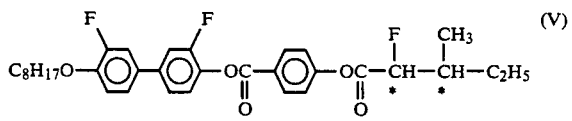
(IV)

(where i, j, k, m, and q each denotes an integer of 1 to 15.)

The mixture of non-chiral liquid crystals was composed of 58 wt % of (A), 22 wt % of (B), and 20 wt % of (C). The mixing ratio of the chiral component [the optically active component (I)]to the non-chiral component [(A)+(B)+(C)] was 5:95 by wt %.

Example 4

The optically active compound (II) was synthesized according to the procedure mentioned in Example 2. Then, it was mixed with a non-chiral component as in Example 3 to give a ferroelectric liquid crystal composition.

Example 5

An optically active compound represented by the formula (III) below was synthesized.

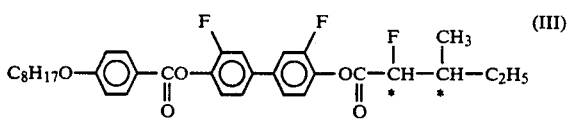
(III)

First, octyloxybenzoic acid was heated in thionyl chloride under reflux until complete dissolution. Excess thionyl chloride was removed by vacuum distillation. Thus there was obtained octyloxybenzoic acid chloride.

Difluorobiphenol was dissolved in dioxane and triethylamine was added to the solution. The resulting solution was added dropwise to the previously prepared octyloxybenzoic acid chloride. After dilution with water, the solution was extracted with chloroform. The extract was freed of chloroform by distillation and the residues were crystallized from ethanol. Crystals of diester compound were filtered off and the filtrate was freed of solvent and the residues (monoester) were crystallized again from ethanol.

The crystals were dissolved in benzene, and to the resulting solution were added triethylamine and then added dropwise a benzene solution of 2-fluoro-3-methylpentanoic acid chloride.

The solution was passed through a silica gel column (n-hexane/chloroform) for separation. Upon recrystallization from ethanol, there was obtained the optically active compound (III).

The optically active compound (III) was mixed with a non-chiral component as in Example 3 to prepare a ferroelectric liquid crystal composition.

Example 6

An optically active compound represented by the formula (IV) below was synthesized by the same procedure as in Example 5 except that the octyloxybenzoic acid was replaced by octylcyclohexanecarboxylic acid.

The optically active compound (IV) was mixed with a non-chiral component as in Example 3 to prepare a ferroelectric liquid crystal composition.

Example 7

An optically active compound represented by the formula (V) below was synthesized in the following manner.

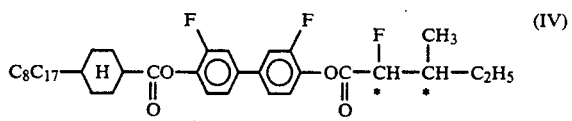
(V)

First, p-hydroxybenzoic acid was dissolved in dioxane. To the resulting solution were added triethylamine and then acetic acid chloride dropwise, followed by stirring for 8 hours. After standing overnight, water was added for crystallization and crystals were filtered off and washed with hexane, followed by vacuum drying at 80° C.

The crystals were dissolved in thionyl chloride and the solution was heated at 50°-60° C. under reflux for 1 hour. Excess thionyl chloride was removed by vacuum distillation. A benzene solution of the acetylbenzoic acid chloride was added dropwise to a benzene solution of octyloxybiphenol containing triethylamine, followed by stirring for 30 minutes. After dilution with water, the solution was extracted with chloroform and ether. The extract was freed of solvent and the residues were recrystallized from ethanol.

The crystals were dissolved in a mixed solvent of tetrahydrofuran and methanol, and the solution was refluxed for 3 hours in the presence of lithium hydroxide. Water was added for crystallization, and the crystals were filtered off and recrystallized from ethanol. The crystals underwent chromatography for separation by a silica gel column (n-hexane/ethanol).

The separated product was dissolved in benzene. To the resulting benzene solution were added triethylamine and then 2-fluoro-3-methylpentanoic acid chloride dropwise.

After standing overnight, the solution was passed through a silica gel column for separation. Upon recrystallization from ethanol, there was obtained the optically active compound (V).

The optically active compound (V) was mixed with a non-chiral component as in Example 3 to prepare a ferroelectric liquid crystal composition.

Example 8

An optically active compound represented by the formula (VI) below was synthesized by the same procedure as in Example 1 except that the decyl chloride was replaced by octyl chloride.

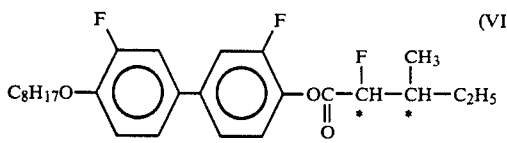

The optically active compound (VI) was mixed with a non-chiral component as in Example 3 to prepare a ferroelectric liquid crystal composition.

The ferroelectric liquid crystal compositions obtained in Examples 3 to 8 were tested for phase transition temperature and spontaneous polarization. The results are shown in Table 1.

TABLE 1

|  | Phase transition temperature [°C.] $I_{SO} \to N^* \to SmA \to SmC^* \to Cr$ | | | | Spontaneous polarization [nC/cm$^2$] |
|---|---|---|---|---|---|
| Example 3 | 103.9 | 92.4 | 74.3 | −26.8 | 13.2 |
| Example 4 | 104.0 | 88.1 | 71.7 | −30.9 | 20.8 |
| Example 5 | 110.0 | 96.7 | 81.5 | −27.8 | 8.69 |
| Example 6 | 110.1 | 99.1 | 77.8 | −26.1 | 11.6 |
| Example 7 | 109.2 | 93.9 | 82.1 | −31.0 | 7.46 |
| Example 8 | 105.5 | 93.5 | 76.5 | −29.5 | 8.85 |

$I_{SO}$: isotropic liquid phase,
N*: chiral nematic phase,
Cr: crystalline phase.

It is noted from Table 1 that the ferroelectric liquid crystal compositions obtained in Example 3 to 8 all have a broad temperature range for the SmC* phase and sufficient spontaneous polarization for practical use. Therefore, it has been demonstrated that an optically active compound which is not satisfactory when used alone can be made into an outstanding ferroelectric liquid crystal composition by mixing it with a non-chiral component.

Example 9

Several kinds of ferroelectric liquid crystal compositions were prepared which contain the optically active compound (I) as the chiral component in varying amounts of 5 wt %, 10 wt %, and 15 wt %. They were tested for phase transition temperature and spontaneous polarization. The results are shown in Table 2.

TABLE 2

| Chiral component [wt %] | Phase transition temperature [°C.] $I_{SO} \to N^* \to SmA \to SmC^* \to Cr$ | | | | Spontaneous polarization [nC/cm$^2$] |
|---|---|---|---|---|---|
| 5 | 103.9 | 92.4 | 74.3 | −26.8 | 13.2 |
| 10 | 100.7 | 89.0 | 69.5 | −29.2 | 28.8 |
| 15 | 98.9 | 97.4 | 65.8 | −29.8 | 32.8 |

Example 10

Several kinds of ferroelectric liquid crystal compositions were prepared which contain the optically active compound (II) as the chiral component in varying amounts of 5 wt %, 10 wt %, and 15 wt %. They were tested for phase transition temperature and spontaneous polarization. The results are shown in Table 3.

TABLE 3

| Chiral component [wt %] | Phase transition temperature [°C.] $I_{SO} \to N^* \to SmA \to SmC^* \to Cr$ | | | | Spontaneous polarization [nC/cm$^2$] |
|---|---|---|---|---|---|
| 5 | 104.0 | 88.1 | 71.7 | −30.9 | 20.8 |
| 10 | 100.1 | 82.2 | 67.3 | −30.6 | 40.5 |
| 15 | 95.7 | 75.9 | 60.0 | −30.7 | 55.3 |

It is noted from Tables 2 and 3 that the ferroelectric liquid crystal compositions have the chiral smectic C phase over a broad temperature range if they contain the non-chiral component in an amount from 1 wt % to 15 wt %. It was also found that the spontaneous polarization of the ferroelectric liquid crystal compositions increases in proportion to the amount of the non-chiral component they contain. The spontaneous polarization reaches the maximum when the content of the chiral component is 15 wt %. It is 32.8 nC/cm$^2$ in the case of the optically active compound (I) and 53.3 nC/cm$^2$ in the case of the optically active compound (II).

Example 11

The ferroelectric liquid crystal compositions were tested for response time by measuring the time required for the light transmittance to change from 0% to 90% when a voltage is applied at room temperature.

This test was carried out using a cell of polyimide resin (with a 2 μm gap), with the substrates arranged antiparallel after rubbing for alignment. In general, a liquid crystal takes on the chevron structure when it is poured into a rubbed cell, and it takes on a pseudo bookshelf structure when an electric field of ±20~30 V (100 Hz) is applied. In this example, measurements were carried out while the liquid crystal takes on the pseudo bookshelf structure. The results for the optically active compound (I) are shown in Table 4. The results for the optically active compound (II) are shown in Table 5.

TABLE 4

| Chiral component [wt %] | Response time [μs] | | |
|---|---|---|---|
|  | ±10 V | ±20 V | ±30 V |
| 5 | 340 | 200 | 165 |
| 10 | 310 | 170 | 105 |
| 15 | 230 | 100 | 62 |

TABLE 5

| Chiral component [wt %] | Response time [μs] | | |
|---|---|---|---|
|  | ±10 V | ±20 V | ±30 V |
| 5 | 430 | 210 | 160 |
| 10 | 300 | 270 | 150 |
| 15 | 215 | 90 | 56 |

In the case where the amount of the chiral component is 15 wt % and a voltage of ±30V is applied, the response time was as short as 62 μs for the optically active compound (I) and as short as 56 μs for the optically active compound (II).

The ferroelectric liquid crystal composition filled in the cell (with a 2 μm gap) was tested for electro-optic effect by measuring the contrast it produces in the memory cycle when it is driven by a pulse of 200 μs, ±20V. The value of contrast was as high as 80.

EFFECT OF THE INVENTION

The present invention provides a ferroelectric liquid crystal composition having a broad temperature range for the chiral smectic C phase, sufficiently great spontaneous polarization, short response time, and high contrast ratio. It is composed of the optically active compound pertaining to the present invention and a non-chiral component.

The ferroelectric liquid crystal composition is superior in response performance to the conventional TN-type liquid crystal devices. Since it produces the memory effect if a proper alignment technique is employed, it will find use as the display device capable of displaying a large amount of information and the high-speed optical shutter which permits quick response and high-density display. Moreover, it is expected to find use in the field of optoelectronics device (such as space light modulator) and image processing device.

What is claimed is:

1. An optically active compound represented by the formula:

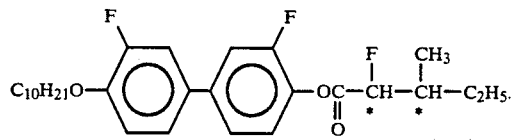

2. An optically active compound represented by the formula:

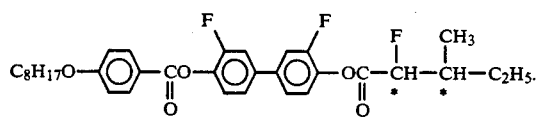

3. An optically active compound represented by the formula:

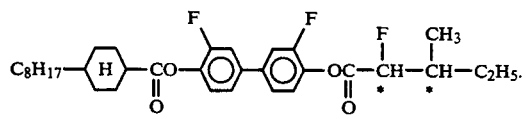

4. An optically active compound represented by the formula:

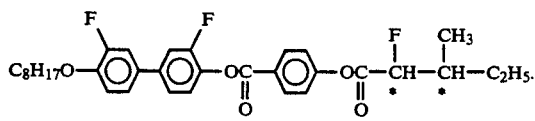

5. An optically active compound represented by the formula:

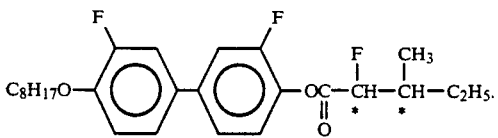

6. A ferroelectric liquid crystal composition comprising chiral an non-chiral components, wherein the chiral component comprises a compound represented by the formula:

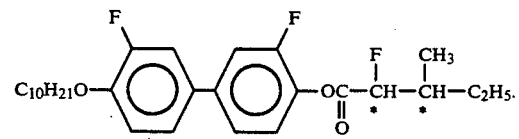

7. A ferroelectric liquid crystal composition chiral and non-chiral components, wherein the chiral component comprises a compound represented by the formula:

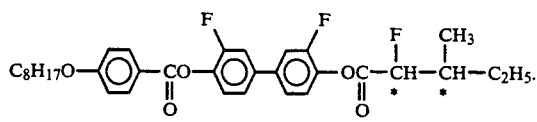

8. A ferroelectric liquid crystal composition comprising chiral and non-chiral components, wherein the chiral component comprises a compound represented by the formula:

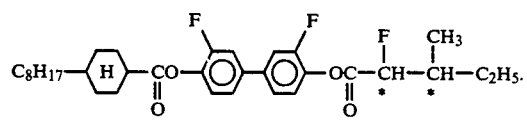

9. A ferroelectric liquid crystal composition comprising chiral and non-chiral components, wherein the chiral component comprises a compound represented by the formula:

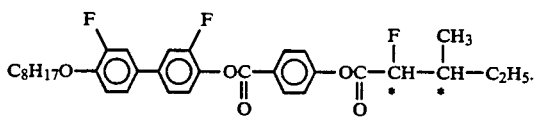

10. A ferroelectric liquid crystal composition comprising chiral and non-chiral components, wherein the chiral component comprises a compound represented by the formula:

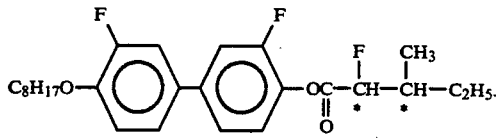

* * * * *